(12) United States Patent
Brawner et al.

(10) Patent No.: US 7,063,669 B2
(45) Date of Patent: Jun. 20, 2006

(54) PORTABLE ELECTRONIC SPIROMETER

(75) Inventors: David Brawner, Zurich (CH); Christopher Hegarty, Oberaegeri (CH)

(73) Assignee: Dynamic MT AG, Oberaegeri (CH)

( * ) Notice: Subject to any disclaimer, the term of this patent is extended or adjusted under 35 U.S.C. 154(b) by 0 days.

(21) Appl. No.: 10/193,922

(22) Filed: Jul. 15, 2002

(65) Prior Publication Data
US 2003/0216659 A1    Nov. 20, 2003

(30) Foreign Application Priority Data
May 16, 2002    (CA)    .................................... 2386639

(51) Int. Cl.
*A61B 5/00*    (2006.01)
(52) U.S. Cl. ...................... 600/533; 600/538
(58) Field of Classification Search ................. 600/538
See application file for complete search history.

(56) References Cited

U.S. PATENT DOCUMENTS

| | | | | |
|---|---|---|---|---|
| 4,127,115 | A | * | 11/1978 | Franetzki .................... 600/538 |
| 4,991,591 | A | | 2/1991 | Jones et al. |
| 5,111,827 | A | | 5/1992 | Rantala |
| 5,137,026 | A | * | 8/1992 | Waterson et al. ........... 600/538 |
| 5,170,798 | A | | 12/1992 | Riker |
| 5,373,851 | A | | 12/1994 | Reinhold, Jr. et al. |
| 5,501,231 | A | | 3/1996 | Kaish |
| 5,518,002 | A | * | 5/1996 | Wolf et al. .................. 600/538 |
| 5,522,397 | A | | 6/1996 | Vermaak |
| 5,562,101 | A | | 10/1996 | Hankinson et al. |
| 5,715,831 | A | * | 2/1998 | Johnson ..................... 600/539 |
| 6,050,953 | A | | 4/2000 | Warwick et al. |
| 6,152,129 | A | * | 11/2000 | Berthon-Jones ........ 128/200.24 |
| 6,190,326 | B1 | | 2/2001 | McKinnon et al. |
| 6,203,502 | B1 | * | 3/2001 | Hilgendorf et al. ......... 600/538 |
| 6,224,560 | B1 | | 5/2001 | Gazula et al. |
| 6,322,519 | B1 | * | 11/2001 | Moulin ....................... 600/538 |
| 6,379,311 | B1 | * | 4/2002 | Gaumond et al. .......... 600/529 |
| 6,626,845 | B1 | * | 9/2003 | Lingo et al. ................ 600/538 |
| 2001/0027274 | A1 | * | 10/2001 | Pompei ...................... 600/474 |

* cited by examiner

*Primary Examiner*—Robert L Nasser
(74) *Attorney, Agent, or Firm*—Vermette & Co.

(57) ABSTRACT

A spirometer having a housing with an elongated flow chamber open at one end, a pressure sensing end opposite the open end and an outlet passageway intercepting the flow chamber at an angle α and proximate the pressure sensing end. A differential pressure sensor is coupled to the pressure sensing end from a port at an angle β to an axis of the flow chamber. The angle α is substantially greater than 0° but substantially less than 180° while the angle β may range from 90° to 180°, such that a significantly increased measured air pressure results over that measured when α=180° and β=90°.

14 Claims, 7 Drawing Sheets

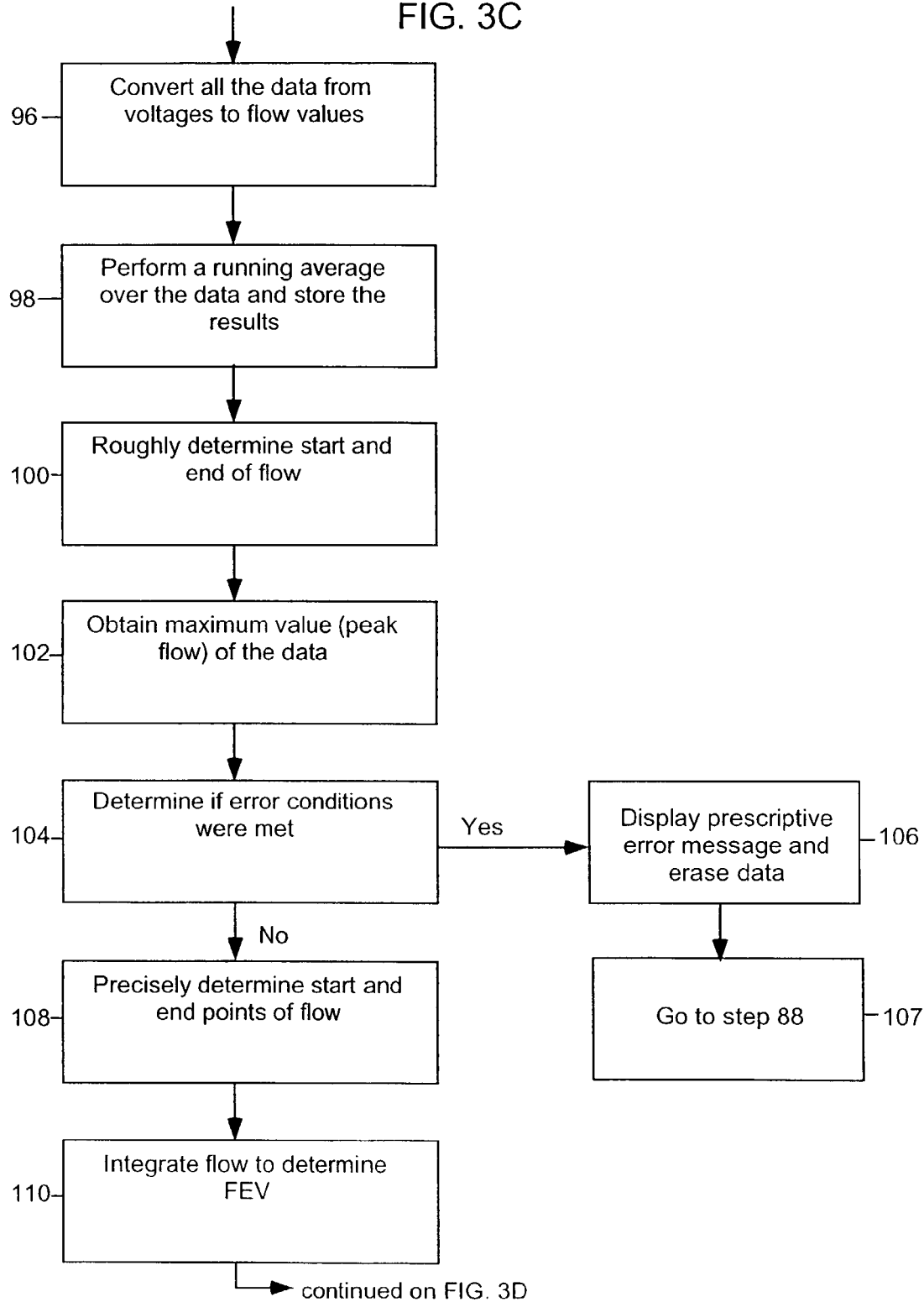

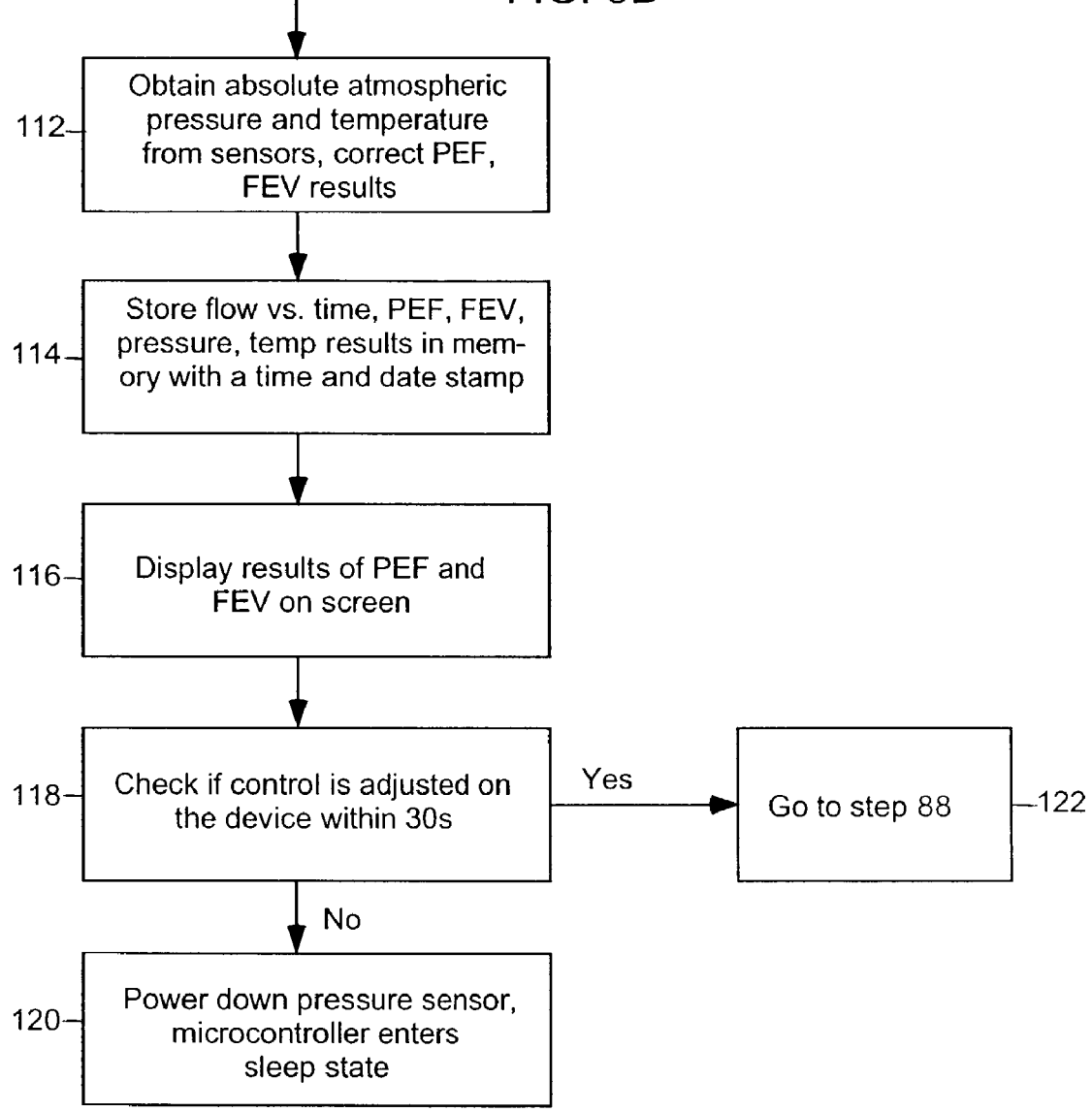

PORTABLE ELECTRONIC SPIROMETER

FIELD

The present invention relates to a portable spirometer for monitoring lung function and for transferring spirometer data to other computers.

BACKGROUND OF THE INVENTION

A spirometer is a device that monitors respiration. A spirometer can be used for the diagnosis and monitoring of pulmonary diseases, particularly asthma and COPD (smoker's cough). Spirometers are also used to monitor the performance of athletes, as well as screen for occupational health problems such as black lung disease or silicosis. Spirometers are generally divided into two classes which have different specifications and purposes. The first class of spirometer are diagnostic spirometers which are used by physicians for the diagnosis of a person's respiratory condition. Diagnostic spirometers must be able to measure many different parameters of respiratory flow and must have a high degree of accuracy. The second class of spirometers are monitoring spirometers which are used to monitor the condition of the lungs on a regular basis. Spirometers used for monitoring must be inexpensive, portable, and easy to use.

Monitoring spirometers usually measure a key parameter called peak respiratory flow or peak expiratory flow (PEF). Peak expiratory flow (hereafter referred to as "peak flow") is defined as the maximum flow rate recorded during a forced expiration of air from the lungs. A person's respiratory condition can be monitored by measuring peak flow with a portable spirometer. Doctors recommend that patients with moderate to severe asthma should record their peak flow on a daily basis to determine the effectiveness of the treatment given to them. This opinion is also supported by the US government sponsored National Heart, Lung, and Blood Institute (NHLBI). When a patient is able to regularly monitor his/her condition, the chances of successful treatment are improved.

Most monitoring spirometers are mechanical devices with a moving vane or rotating wheel that record the air flow caused by a person's expiration into the spirometer. While these spirometers are inexpensive and, therefore widely used, they suffer from certain disadvantages. Typically, these spirometers have a low level of accuracy due to friction and other artefacts of their mechanical construction. Other limitations arise because the inertia of the mechanical vane or wheel prevents a reliable flow measurement as a function of time, and so the spirometers are only capable of measuring an approximation of the peak flow. In addition, ordinarily such spirometers have no means of recording and transmitting the results in electronic form. This means that the patient must record results manually. In some cases, electronic sensing is used to record the motion of a vane or wheel, and the results can be stored internally or sent electronically to remote computers. However, the underlying mechanical means of flow measurement prevents a highly accurate or complete determination of the flow properties.

In order to determine if a peak flow result from a monitoring spirometer is reliable, it is necessary to observe the overall flow versus time during the entire breathing manoeuvre. If a user does not use a correct breathing technique, coughs, or does not exhale forcefully enough, the peak flow meter will have an inaccurate result. Only by observing the resulting flow versus time data would a physician be able to determine if the particular manoeuvre was acceptable. Because of the limitations described above, existing mechanical monitoring spirometers are not able to make this determination.

Some purely electronic spirometers (pneumotachographs) were developed which calculate the air flow from a pressure difference measured across an obstruction in the flow channel. Most often, a differential pressure sensor is connected to two outlets on the flow channel on either side of the flow obstruction. The obstruction may be a restriction in the flow channel or a fine wire mesh or ceramic screen. These spirometers are an improvement over the mechanical spirometers but still have certain drawbacks. The restriction or screen may trap contaminants from the user's breath which could alter the flow properties of the spirometer. These contaminants may also spread disease from one user to another and the spirometer must be carefully sterilized. The ports in the flow channel that connect to the pressure sensors must be kept clear of contaminants that impede the flow and could damage the sensor. Sterilization of the ports must also be possible without damaging the pressure sensors. For these reasons many pneumotachographs provide filters or membranes to protect the sensors, but these add to the complexity of the spirometer and reduce its sensitivity to air flow. The pressure transducers, which are used to sense the pressure on either side of the restriction, are often of an expensive design making them too costly to be used widely as monitoring spirometers. For the most part, pneumotachographs are sold as diagnostic spirometers for use by medical professionals rather than by the general public.

The pneumotachographs intended for portable monitoring typically calculate, store, and display on an LCD display only the value of the peak flow. This limitation results because the processors and memory used in these electronic spirometers have a limited processing speed and size, and are unable to make accurate determination of flow versus time in real time. A hardwired ROM memory on such pneumotachographs is an additional drawback because it requires physical replacement of the memory spirometer to accommodate an improved or customized data acquisition algorithm. The data are also stored in RAM memory and, as a result, are lost when power is interrupted. Due to the low sensitivity of the spirometer, heavy analog filtering is required. Such filtering lowers the time response of the spirometer, and results in less accurate data being recorded.

To be of any value, the results obtained from a spirometry measurement require a proper effort and technique from the user during the forced expiration. A peak flow result obtained with the wrong technique is useless, and so the technique used must be monitored. Preferably, a doctor should be able to view the entire flow versus time chart to determine if the technique was correct and, hence, whether or not the flow result should be considered.

Advances in microprocessor and memory technology as well as improved solid state pressure sensors enable new monitoring spirometers with improved features and lower cost. New spirometers using EEPROM (flash) memory would permit the remote programming of the spirometers. This would allow practitioners to adapt their algorithm for the flow measurement to best suit individual conditions and even individual users. With the rise of the internet and desktop computing, a spirometer designed to be interfaced with a portable computer is also highly desirable and should improve patient care and monitoring possibilities.

The flow rate and flow volume results obtained by pneumotachographs are dependent on local temperature and atmospheric pressure. The local atmospheric pressure varies on the order of 10% due to weather fluctuations and may change even more significantly due to the elevation (e.g., there is an 18% air pressure variation between sea-level in San Francisco and Boulder, Colo. at 1,500 m). Few spirometers correct for this automatically, and a manual correction must usually be done after an independent measurement of the local pressure and temperature. If the spirometer is to be used by a patient at home this type of manual correction is not convenient or practical.

There is a clear need for a purely electronic monitoring spirometer that provides reliable results with a low cost design. The design should be as simple as possible to reduce the effects of contamination and allow sterilization. The spirometer should be sufficiently easy to use for patients themselves to perform home monitoring. It should not require extensive maintenance. The spirometer should also be capable of interfacing with a desktop computer or the internet to allow convenient data collection. Collection of the entire flow versus time waveform is also desirable so that medical professionals can check the reliability of the results. An optional additional feature of such a spirometer would be a feature that measures the local temperature and atmospheric pressure and makes an automatic correction of the results. Such a feature would provide a significant enhancement of the spirometer's accuracy

SUMMARY OF THE INVENTION

According to the invention there is provided a spirometer having a housing with an elongated flow chamber open at one end, a pressure sensing end opposite the open end and an outlet passageway intercepting the flow chamber at an angle • and proximate the pressure sensing end. A differential pressure sensor is coupled to the pressure sensing end from a port at an angle • to an axis of the flow chamber. The angle • is substantially greater than 0° but substantially less than 180° while the angle • may take any value between 90° and 180°, such that a significantly increased measured air pressure results over that measured when $\alpha=180°$ and $•=90°$.

Preferably, the differential pressure sensor is coupled to the pressure sensor by a meander passageway through which only diffusion of air takes place and whose length divided by the speed of sound is less than the measuring rate of the differential pressure sensor.

The meander passageway is bent to inhibit contaminants blown into the flow chamber from reaching the differential pressure sensor. A rigid meander passageway is advantageous to prevent errors in the signal due to passageway flexing or motion.

Advantageously, the angle • is 90° and the angle •• is 180°.

Preferably the flow chamber has an elliptical cross-section.

The flow chamber and meander passageway may be detachable from the differential pressure sensor and electronics to facilitate sterilization.

The rate of measurement by the pressure sensor is sufficiently high to obtain a complete flow rate versus time curve.

The portable, fully electronic spirometer using a pneumotachography technique described here uses a single pressure sensor to sense the flow of air through a specially designed flow channel. This channel has a slight restriction in diameter at the flow outlet, which causes an increase in pressure inside as air flows through it. This air pressure rise can be measured with a single pressure sensor that is connected to the spirometer. The flow outlet, and pressure sensor are positioned at angles to the flow such that the increase in pressure measured by the sensor is optimized. This novel feature can enhance the change in differential pressure measured by the sensor by an order of magnitude over prior art spirometers, increasing accuracy substantially.

The flow channel is designed to be detachable from the pressure sensor and associated electronics to facilitate cleaning and sterilization. In the invention described here, only one passage is used to connect the pressure sensor with the flow chamber, reducing cost and complexity. Any reduction in the complexity of the flow chamber is desirable as this will reduce the building up of contaminants and simplify sterilization of the spirometer.

During a user expiration, the electrical signals from the pressure sensor are amplified, converted from analog to digital by an A/D converter, and stored in memory by a microprocessor. The spirometer stores the complete flow time data for up to 50 sample expirations along with a time/date stamp. The spirometer is capable of performing an analysis for each expiration and will display these results on an LCD display. The spirometer is able to determine whether an expiration was performed with a correct breathing technique or not, and alert the user immediately if the expiration is questionable. The electronics are battery powered for portability and contain features to control the consumption of power to prolong battery life. Interfacing with an external computer is also possible, permitting the user to transfer data from the spirometer and display the results on a larger external screen with additional software. Since the data from the entire flow is captured by the spirometer, additional analysis may also be done on the data, either within the spirometer itself or on an external computer.

Absolute pressure and temperature sensors are added to the spirometer to measure the local environmental operating conditions during the measurement. These results are recorded by the microcontroller and stored with the data, allowing an automatic correction of the spirometer results. This can result in improved accuracy and reproducibility.

All data are stored in EEPROM memory, which is capable of retaining the data in the event that electrical power is interrupted. Since the microcontroller program is also stored in EEPROM memory, this program may be changed, customized or updated as needed whenever the spirometer is connected to a PC operating the appropriate software. A typical operating sequence for the spirometer would be a program to acquire the flow data, compute and display the peak flow as well as the FEV1 (forced expiratory volume after one second). The program should also permit the transfer of data to an external computer and an update of the software for the microcontroller.

BRIEF DESCRIPTION OF THE DRAWINGS

Further features and advantages will be apparent from the following detailed description, given by way of example, of a preferred embodiment taken in conjunction with the accompanying drawings, wherein:

FIGS. 3A–D are flow diagrams corresponding to the operation of the microcontroller program of the spirometer.

DETAILED DESCRIPTION WITH REFERENCE TO THE DRAWINGS

Spirometer Construction

Figure 1:
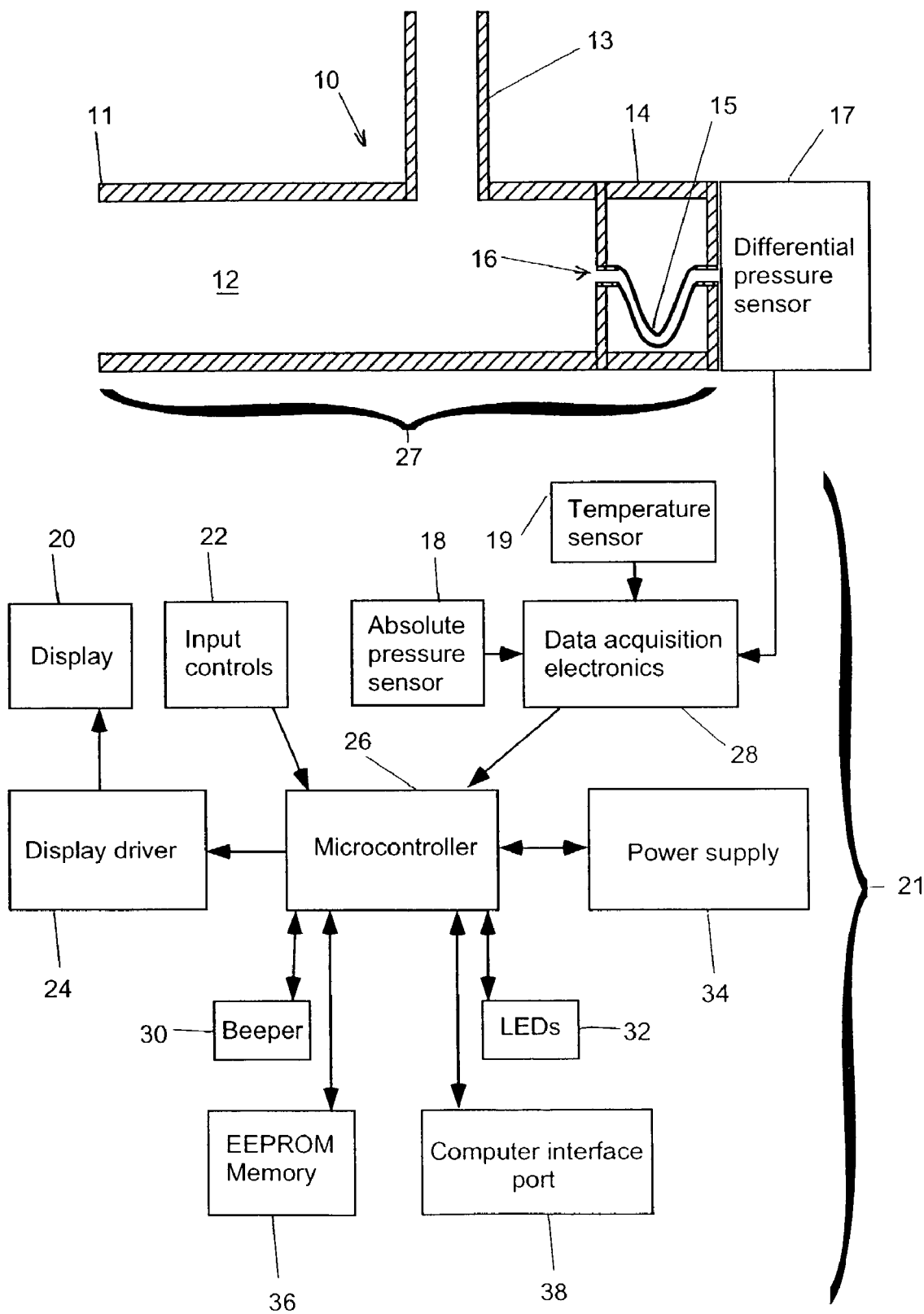
FIG. 1. is a cross sectional view of the spirometer with accompanying electronics shown in schematic form.

Referring to FIG. 1, the spirometer 10 consists of a housing 27 having a flow chamber 12, with a mouthpiece 11 and a meander passageway structure 61. The meander passageway structure 61 consists of a housing compartment 14 having end walls 63 and 65 at opposite ends and a hollow meander tube 15 whose meander passageway 16 is bent and opens through end walls 63 and 65 to provide fluid communication between the flow chamber 12 and a differential pressure sensor 17. The meander tube 15 could be replaced by, for example, a block of material with a bore therethrough. A differential pressure sensor 17 is located at an end of the flow chamber 12 opposite the mouthpiece 11. The meander tube 15 is used to protect the pressure sensor 17 from the direct flow of air so that contaminants from a user's breath will not enter the pressure sensor 17. An outlet tube 13 intersects the flow chamber 12 transversely. The meander tube 15 and crosshatched area may be constructed from a tube of metal such as stainless steel. A more cost effective construction for mass production (e.g., pressure moulding) may be used to form the meander passageway 16 rather than a stainless steel tube. The only requirement is that there is a dead air space in the passageway that presents an obstacle to the ballistic flow of contaminants. Electronics 21 are coupled to the differential pressure sensor 17 and are operative to process the pressure data. The pressure sensor 17 and electronics 21 are detachable from the rest of the spirometer 10. This enables convenient sterilization and cleaning of the spirometer 10 in the event that there are multiple users of the spirometer. An alternative to sterilization is to simply dispose of the housing 27 and replace it with a new one. The ability to detach the housing 27 also serves to protect the more costly pressure sensor 17 and electronics 21 from the sterilization process.

Data acquisition electronics 28 (e.g., differential amplifier, ADC (not shown)) has an input coupled to the differential pressure sensor 17 and receives pressure data from the latter. Another input of the data acquisition electronics 28 is coupled to a temperature sensor 19 and receives temperature data. Finally the data acquisition electronics 28 are also coupled to the absolute pressure sensor 18 and receives ambient pressure data from the latter. The ambient pressure and temperature data are used to correct volume and flow rate results. The data acquisition electronics outputs digital signals to the microcontroller 26. The microcontroller 26 is also coupled to an input control module which accepts inputs from a user and transfers corresponding digital signals to the microcontroller 26. A power supply 34 provides and controls electrical power to the sensors 17,18, and 19 and to the rest of the electronics 21. An operating program is stored in the EEPROM memory 36 which is coupled to the microcontroller 26. The EEPROM memory 36 also stores data from the differential pressure sensor 17 even when there is no power. A computer interface port 38 couples to the microcontroller 26 and permits interfacing with an external computer (not shown). A display 20 couples to the microcontroller 26 through display driver 24 and displays results on a display screen. A set of input controls 22 also connect to the microcontroller 26 and provide user access to the system. A beeper 30 coupled to the microcontroller 26 provides audible signals as prescribed by the algorithm controlling the EEPROM 36. LED's 32 provide additional display capability.

Figure 2A:
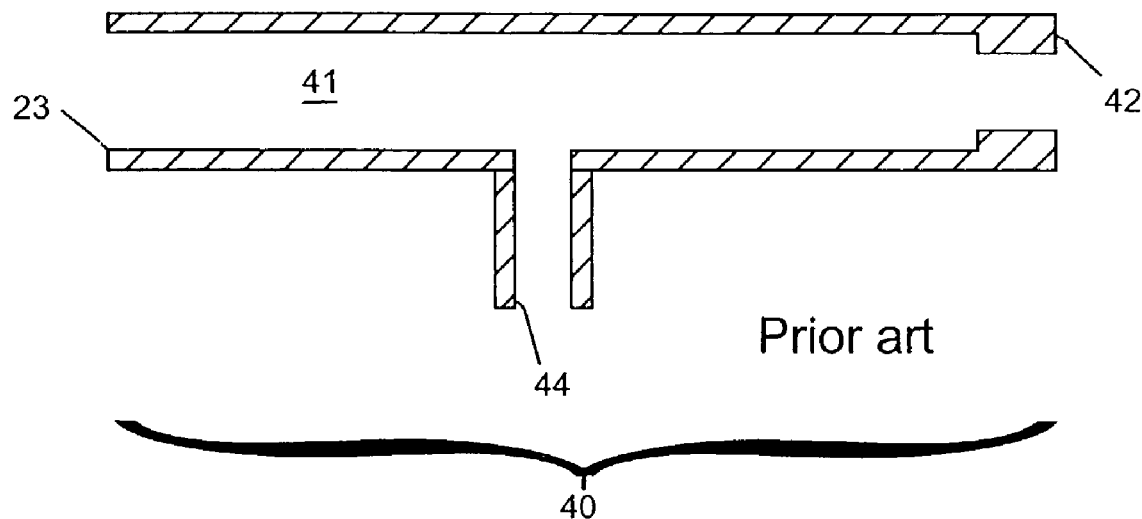
FIG. 2A is a cross sectional view of a spirometer according to the prior art.
Figure 2B:
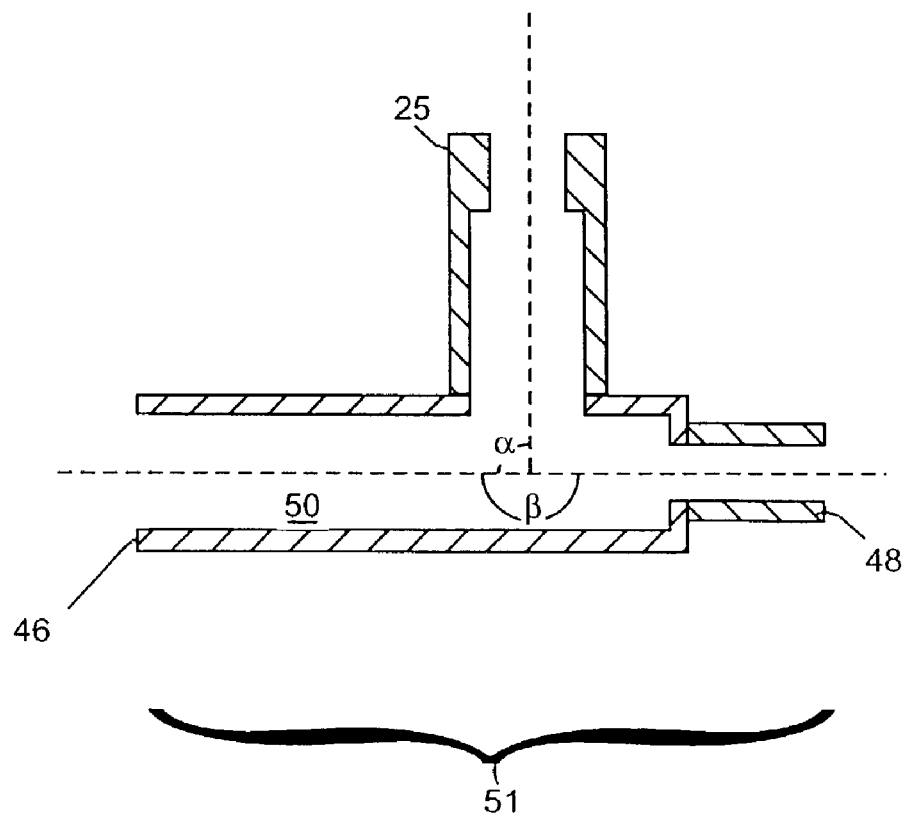
FIG. 2B is a cross-sectional view of the present spirometer.
Figure 3A:
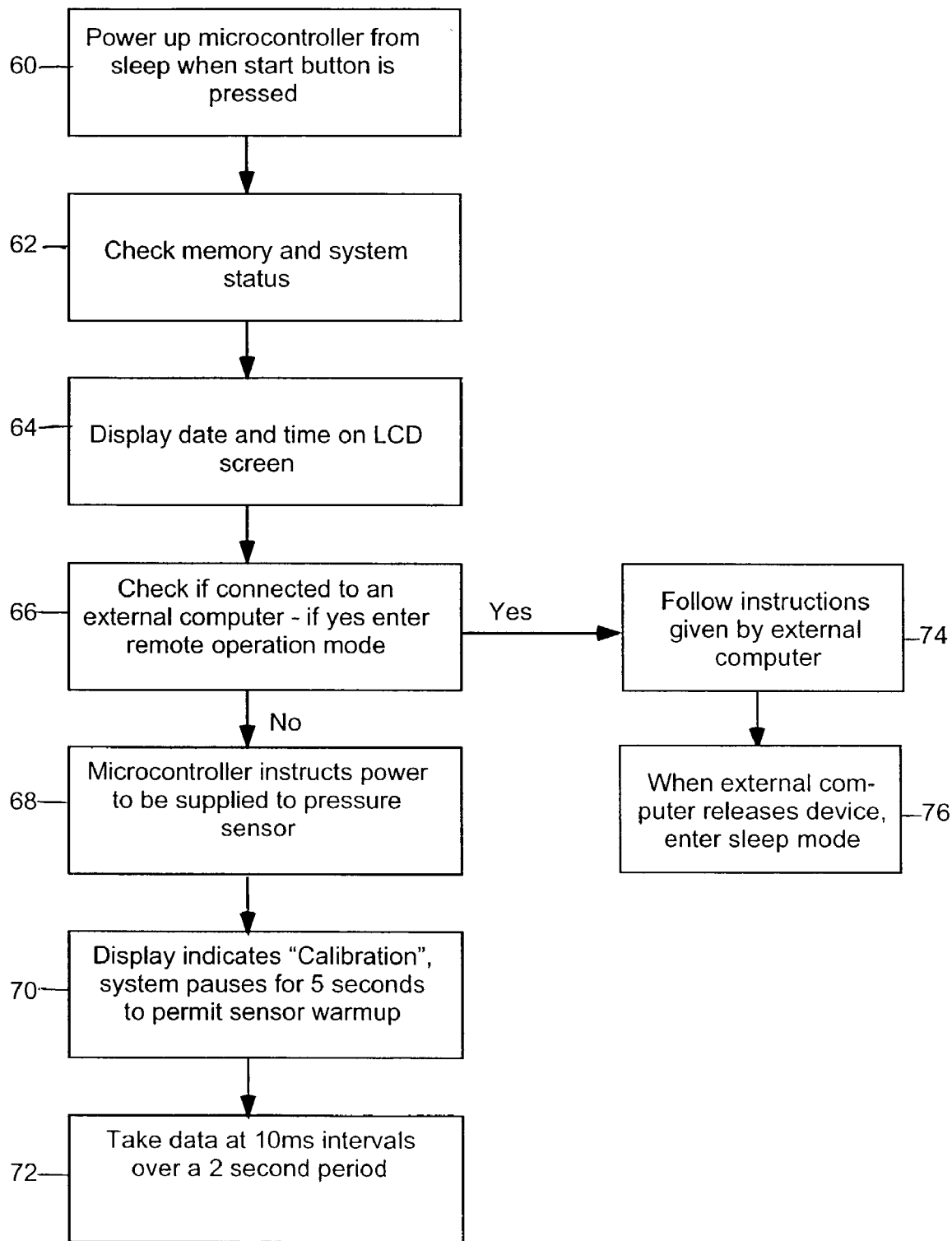
Figure 3B:
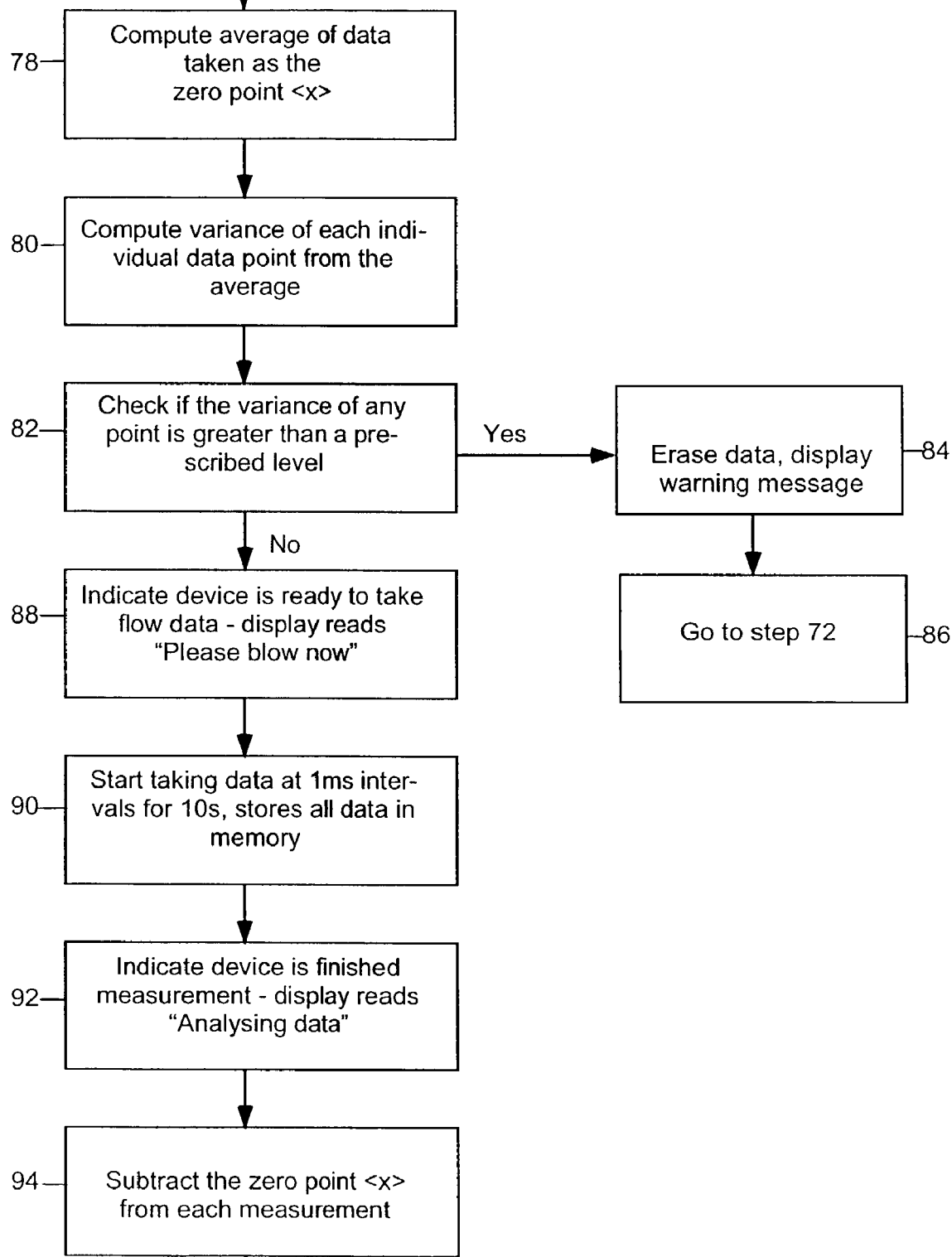

Referring to FIG. 2A a known spirometer has a housing 40 with a mouthpiece 23 at one end of a flow chamber 41, an outlet 42 at the other end and a port to measure the pressure 44 at 90° to the axis of the flow chamber 41. In contrast the present spirometer has a housing 51 with a flow chamber 50, an outlet 25 at right angles to the flow chamber 50 and a pressure sensing end 48 opposite a mouthpiece 46.

The two flow chamber geometries are identical when the angles $\alpha=180°$ and $\beta=90°$. It was found that if the angles were changed from the latter, the pressure measured at port 48 could be significantly increased by approximately an order of magnitude. Such an increase enables a much greater signal-to-noise ratio and a higher accuracy in the measurement. The exact increase is heavily dependent on the precise size and geometry of the flow chamber 50 and angles. In general the flow is enhanced when the angle $\alpha$ is greater than 0° but less than 180° and when $\beta$ has a value between 90° and 180°. For the preferred embodiment, the angles were chosen as $\alpha=90°$ and $\beta=180°$ for reasons of convenience of use, manufacture, and significantly increased measured pressure as a function of flow. The use of this novel geometry increases the signal-to-noise ratio of the flow measurement significantly, and enables a much higher measurement precision.

The principle purpose of the meander tube 15 is to protect the pressure sensor 17 from airborne contaminants from a user's breath. Since the air in the meander tube 15 is not set into laminar flow during spirometer operation, airborne contaminants can only reach the pressure sensor 17 by a diffusion process. This diffusion process permits contaminants to reach the pressure sensor 17 at a rate that decays exponentially with the distance along the passageway of the meander tube 15. The transfer of contaminants can thus be minimized by increasing the length of the meander tube 15. For larger contaminants, decreasing the diameter of the passageway of the meander tube 15 will also reduce the rate of penetration of such contaminants to the pressure sensor 17, but a diameter that is too small will begin to complicate an effective cleaning process. If diffusion were the only consideration, in principle the meander tube 15 could be a several meter long flexible tube that connects the pressure sensor 17 to the flow chamber 12, but this leads to several disadvantages. Any motion or flexing of the meander tube 15 during the measurement will influence the pressure measured by the pressure sensor 17. The volume of the meander tube 15 should be kept to a minimum in order to minimize timing errors in the measurement, particularly if the length of the passageway divided by the speed of sound is of the order of the measuring rate of approximately 1 ms. Compressibility of the air in the meander tube 15 will cause an error in the accurate measurement of the pressure in the flow chamber 12 that is proportional to the volume of air in the meander tube 15. An optimal balance of all these considerations leads to a preferred embodiment with a rigid meander tube 15 having an internal diameter of approximately 5 mm and a few cm in length. The diameter could be anywhere in the range of 0.1 mm up to about 10 mm. It is obvious that the meander tube 15 could be replaced by a solid block having an identical passageway 16.

In operation, the pressure sensor 17 provides a voltage signal that may be converted to a digital signal by data acquisition electronics 28 consisting of a differential amplifier with an analog to digital converter (not shown) An A/D conversion rate of 10 bits is used since it provides a resolution at low flows that is roughly the noise level of the measurement. No filtering techniques have been used as they were found to distort the waveform in a way that led to significant errors in peak flow measurement. Instead a digital signal processing technique may be used as specified in the microcontroller program. This leads to the additional benefit that the filtering algorithm can be easily altered by adjusting the microcontroller program.

The microcontroller 26 (e.g., PIC 16F877) is used to direct all electronic operations of the device. Data can be read from the differential pressure sensor 17 and stored directly in EEPROM memory 36. EEPROM memory is used as it is non-volatile and stores the data even when power is not available. The microcontroller program is also stored in EEPROM memory 36, which allows the device to be reprogrammed at will to suit the purpose at hand. The computer interface port 38 is attached to the microcontroller 26 to enable the transfer of data to an external computer (not shown), the reprogramming of the microcontroller instruction set, as well as enable the remote control of the entire device by an external computer (not shown). Results of the measurements can also be processed by a driver 24 for a LCD display 20. Additional display items such as LEDs 32 and a beeper device 30 are also used and controlled by the microcontroller 26.

During a spirometry measurement, the gas expelled by a user cools rapidly and contracts due to the lower ambient temperature and humidity outside of the user's body. Traditionally the volume and flow rate results are corrected for manually by using the body temperature and pressure saturated (BTPS) formula. Conversion factors for this formula are widely available and require knowledge of the ambient absolute pressure and temperature. To enable an automatic correction for these effects, an absolute pressure sensor 18, and temperature sensor 19 are also included. The microcontroller 26 instructs a power supply 34 to regulate the power supplied to the pressure and temperature sensors 17, 18, 19 and to all of the device electronics. This regulation enhances the lifetime of the spirometer under battery operation.

The exact relationship between flow in the flow chamber 12 and the pressure measured at the end wall 63 is highly dependent on the geometry of the spirometer. In this embodiment, the flow outlet 13 compels the flow to exit the flow chamber 12 in a direction perpendicular to the incoming flow. This geometry was found to increase the pressure measured by the pressure sensor 17 by over an order of magnitude when compared to measuring the pressure at an outlet perpendicular to the flow as in FIG. 2A.

The general measurement principle is based on the Venturi effect and the pressure measured is roughly proportional to the square root of the flow. The observed pressure, P, can be accurately modeled with an expansion in the air flow F $$P \approx aF + bF^2 + cF^3,$$

where the dominant term is b. The exact calibration of the desired chamber flow versus pressure relationship may be done by applying known flow rates and measuring the pressure with a manometer. The parameters a, b, c may then be determined by fitting the above equation to the results of the calibration. This fitting is unique for each specific spirometer geometry and need only be done once.

Steps of Operation

The steps used in spirometer operation are shown in FIGS. 3A–3D. The steps here simply reflect a preferred embodiment to suit one particular operating purpose. The design of the spirometer includes EEPROM memory 36 and remote computer connection. At the start of operations the spirometer 10 is generally in the "sleep" state where very little power is consumed. The microcontroller 26 keeps track of the time and date with greatly reduced power consumption to conserve battery power. At 60 the user activates the spirometer 10 by pressing a start control (not shown); full power is then applied to the microcontroller 26. At 62 memory is tested and the program is loaded. The time and date are also displayed on the LCD display 20. At 66 a test is made by the microcontroller 26 to determine if an external computer is connected to the spirometer 10. If an external computer is connected then at 74 control is passed to the external computer (e.g., to download samples or to update the program in the microcontroller 26). Once the external computer relinquishes control, at 76 the spirometer 10 enters a sleep mode. If no external computer is connected, at 68 the microcontroller 26 powers up the pressure sensors 17 and 18 and the temperature sensor 19. In order to conserve battery power, power to the sensors 17, 18 and 19 is applied only when a measurement is being taken. Since a few seconds are required for the sensors to stabilize, at 70 a calibration message is displayed on the LCD display. For the last two seconds of this warm-up period, at 72 a "zero" or ambient level data is taken from the differential pressure sensor 17, and at 78 an average result for "zero" is taken and stored. To check that the spirometer 10 is operating properly, and that there was no airflow passing through the flow chamber 12, at 80 the variance of these "zero" points is taken. At 82 if the variance of the zero data exceeds a specified limit, the data is considered invalid, and at 84 the zeroing process is repeated by erasing the stored data and at step 86 moving back to step 72.

If the variance is acceptable, at step 88 the user is alerted that he/she may blow into the spirometer. At step 90 pressure data is taken at a predefined rate for as long as the user is blowing into the spirometer 10, or for a maximum of 10 seconds and is stored in the EEPROM memory 36. At the end of the expiration the data collection is stopped and at step 92 the user is alerted that the spirometer 10 is analysing the data. At 94 the previously obtained zero point is subtracted from each data point to eliminate any zeroing error in the measurement and at step 96 the data is converted into flow values using a look-up table process with pre-calculated values. In order to smooth out the data, at 98 a running average is taken such that the averaged time scale is still less than what is considered a relevant time scale for lung function measurements (typically 10 ms). At step 100, the start and end point of the flow is determined roughly as the point where the measured flow rate exceeds a set limit. A similar process is then done to determine the exact end point of the flow. At 102 the data between the start and end points is reviewed and the flow point with the peak value is selected as the PEF value. At step 104 error checking of the data is performed. Typical error conditions would be the detection of more than one start and end points or no start and end points at all, or a PEF value that is lower than a specified limit. If errors are detected then at 106, the user is notified and the spirometer returns to step 88. If no errors were detected in the data the analysis process continues. At step 108 a back linear interpolation is done to determine the exact starting point of the flow, and an analogous process is done to determine the end point of the flow sample. At step 110 the flows between the start and end points are integrated to determine FEV values, up to the desired times, e g., 1s for FEV1. At step 112 the voltage from each of the absolute pressure sensor 18 and the temperature sensor 19 is recorded by the spirometer 10, and the BTPS correction factor for the data is determined, stored, and the data is corrected for BTPS. At step 114 all the relevant data for the flow is stored in EEPROM 36 as well as the time, date, absolute pressure, temperature, and all calculated and measured data associated with this flow A summary of the results is displayed at step 116 for the user to observe. At step 118 the measurement cycle is complete, and the spirometer 10 waits to be alerted if it should measure data again. If the user signals the spirometer 10 within 30s to repeat the measurement the program will restart at step 88. If the user does not signal the spirometer 10 to repeat a measurement within a 30s period, at step 120 the spirometer 10 will re-enter the sleep mode and the sensors and electronics will be powered down.

Figure 4:
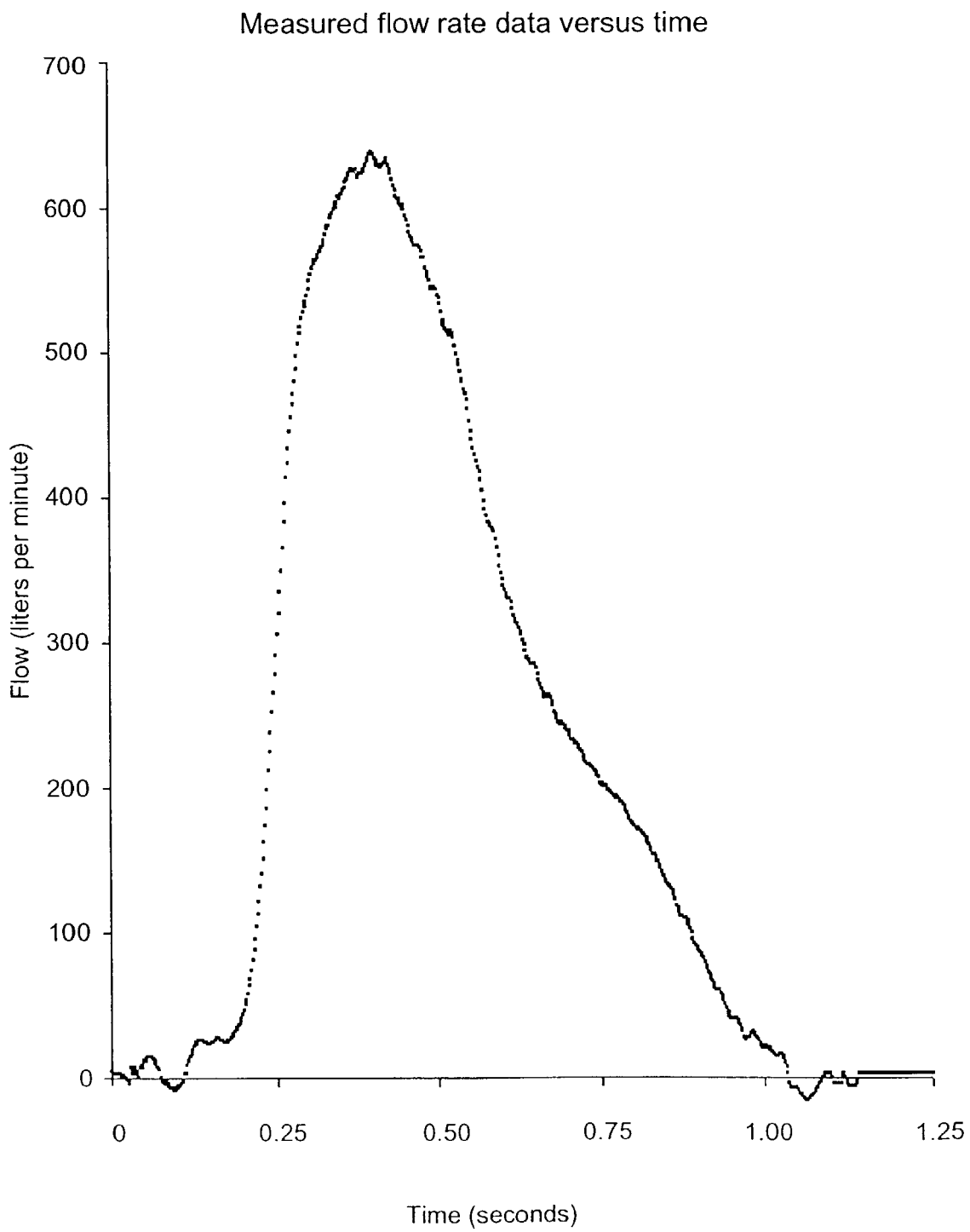
FIG. 4. is a graph of flow versus time for the present spirometer.

A sample of the flow data that is stored by the spirometer 10 is shown in FIG. 4. As can be seen at the start and end points, the noise is greatest due to the nature of the flow/pressure relationship. The effect of a user moving the spirometer 10 towards the mouth for a breath can also cause a significant measurement as well as any slight exhalation or inhalation. This reinforces the need for careful error checking as is described in step 104. Depending on the particular condition of the user, the error checking features will need to be customized. If, for example, the user suffers from COPD, a slower rise of the flow rate will be observed and features in the profile may indicate coughing. The parameters must be carefully determined to check that they do not too frequently reject data from a user that is genuine. The storage of a complete profile in memory permits a doctor to analyse the flow pattern manually and determine if it is clinically useful. A key feature of the spirometer is the ability to easily customize the exact measurement sequence and error checking profiles for a specific user by connection with an external computer.

We claim:

1. A spirometer, comprising:
   a. a housing having an elongated flow chamber at one end, a pressure sensing end opposite said one end, and an outlet passageway intercepting said flow chamber at an angle $\alpha$;
   b. a differential pressure sensor coupled to said pressure sensing end of said flow chamber at an angle $\beta$ to an axis along a length of said flow chamber, said differential pressure sensor closed to air flow therethrough, said differential pressure sensor is coupled to said flow chamber by meander passageway through which only diffusion of air takes place and whose length divided by the speed of sound is less than a measuring rate of said differential sensor and said meander passageway is bent to inhibit contaminants from said flow chamber from reaching said differential pressure sensor;
   wherein said angle $\alpha$ is substantially greater than 0° but substantially less than 180° and wherein said angle $\beta$ is equal to or greater than 90° and less than or equal to 180°.

2. A spirometer according to claim 1, wherein said spirometer is portable.

3. A spirometer according to claim 1, wherein $\alpha$ is 90° and $\beta$ is 180°.

4. A spirometer according to claim 1, wherein said flow chamber has an elliptical cross-section.

5. A spirometer according to claim 1, wherein said differential pressure sensor is detachable from said spirometer housing to permit sterilization of said spirometer housing.

6. A spirometer according to claim 1, wherein said pressure sensor measures an entire flow versus time curve for an expiration.

7. A spirometer according to claim 1, wherein a diameter of the flow chamber is greater than a diameter of said outlet chamber.

8. A spirometer according to claim 1, having data acquisition and processing electronics coupled to said differential pressure sensor.

9. A spirometer according to claim 1, wherein said electronics includes a EEPROM memory for storing an operating program, flow rate data and time stamp values corresponding to said flow rate data.

10. A spirometer according to claim 9, including a computer interface port for coupling to an external computer to provide access by said external computer to flow rate data and time stamp values stored in said EEPROM memory.

11. A spirometer according to claim 1, including an absolute pressure sensor and temperature sensor coupled to said data acquisition and processing electronics.

12. A spirometer according to claim 1, comprising:
   a. a microcontroller coupled to an output of said pressure sensor;
   b. EEPROM memory coupled to said microcontroller operative to store a program for operating said microcontroller, flow rate data and time stamp values corresponding to said flow rate data; and
   c. an absolute pressure sensor and a temperature sensor operative to provide measurements of local atmospheric pressure and temperature for use in automatically correcting.

13. A spirometer according to claim 1, including a computer interface port coupled to said microcontroller operative to provide external access to the flow rate data and time stamp values stored in said EEPROM memory.

14. A spirometer according to claim 1, in which said outlet passageway is situated proximate said pressure sensing end.

* * * * *

UNITED STATES PATENT AND TRADEMARK OFFICE
CERTIFICATE OF CORRECTION

PATENT NO. : 7,063,669 B2  
APPLICATION NO. : 10/193922  
DATED : June 20, 2006  
INVENTOR(S) : David Brawner and Christopher Hegarty It is certified that error appears in the above-identified patent and that said Letters Patent is hereby corrected as shown below:

Col. 3, Line 34, replace "•" with --α--
Col. 3, Line 36, replace "•" with --β--
Col. 3, Line 37, replace "•" with --α--
Col. 3, Line 38, replace "•" with --β--
Col. 3, Line 40, replace "•" with --β--
Col. 3, Line 51, replace "•" with --α--
Col. 3, Line 51, replace "•" with --β--
Col. 3, Line 66, replace "LED'S" with --LEDS--

Signed and Sealed this

Nineteenth Day of December, 2006

JON W. DUDAS  
*Director of the United States Patent and Trademark Office*